United States Patent
Meadows

(10) Patent No.: US 8,504,163 B1
(45) Date of Patent: Aug. 6, 2013

(54) CRANIALLY MOUNTED STIMULATION SYSTEMS AND METHODS

(75) Inventor: Paul M. Meadows, Glendale, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 1061 days.

(21) Appl. No.: 11/479,707

(22) Filed: Jun. 30, 2006

(51) Int. Cl.
*A61N 1/02* (2006.01)

(52) U.S. Cl.
USPC .......................................................... 607/57

(58) Field of Classification Search
USPC .............................. 607/1, 2, 45–46, 115, 116
See application file for complete search history.

(56) References Cited

U.S. PATENT DOCUMENTS

| | | |
|---|---|---|
| 3,760,984 A | 9/1973 | Theeuwes |
| 3,845,770 A | 11/1974 | Theeuwes et al. |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,203,440 A | 5/1980 | Theeuwes |
| 4,203,442 A | 5/1980 | Michaels |
| 4,210,139 A | 7/1980 | Higuchi |
| 4,327,725 A | 5/1982 | Cortese et al. |
| 4,360,019 A | 11/1982 | Portner et al. |
| 4,487,603 A | 12/1984 | Harris |
| 4,562,751 A | 1/1986 | Nason et al. |
| 4,627,850 A | 12/1986 | Deters et al. |
| 4,678,408 A | 7/1987 | Nason et al. |
| 4,685,903 A | 8/1987 | Cable et al. |
| 4,692,147 A | 9/1987 | Duggan |
| 4,725,852 A | 2/1988 | Gamblin et al. |
| 4,865,845 A | 9/1989 | Eckenhoff et al. |
| RE33,170 E * | 2/1990 | Byers ............................... 607/57 |
| 5,057,318 A | 10/1991 | Magruder et al. |
| 5,059,423 A | 10/1991 | Magruder et al. |
| 5,080,653 A | 1/1992 | Voss et al. |
| 5,097,122 A | 3/1992 | Colman et al. |
| 5,112,614 A | 5/1992 | Magruder et al. |
| 5,137,727 A | 8/1992 | Eckenhoff |

(Continued)

OTHER PUBLICATIONS

U.S. Appl. No. 10/918,978, filed Aug. 16, 2004, Meadows et al., Anchor Device.

(Continued)

*Primary Examiner* — Rex R Holmes
(74) *Attorney, Agent, or Firm* — Vista IP Law Group LLP

(57) ABSTRACT

An exemplary system includes a stimulator with a hollow lumen extending therethrough and configured to be at least partially disposed within a burr hole in a cranium of a patient, a stimulating member configured to apply a stimulus to a stimulation site within the patient, and coupling member configured to extend at least partially through the lumen and couple the stimulating member to the stimulator. Exemplary methods of applying at least one stimulus to a stimulation site within a patient include implanting a lead with a number of electrodes disposed thereon within a cavity formed by a cranium, implanting a stimulator such that the stimulator is at least partially disposed within a burr hole in the cranium, removably coupling the lead to the stimulator, and applying the at least one stimulus to a stimulation site within the cavity formed by the cranium via one or more of the electrodes.

18 Claims, 8 Drawing Sheets

U.S. PATENT DOCUMENTS

| | | | |
|---|---|---|---|
| 5,193,539 A | 3/1993 | Schulman et al. | |
| 5,193,540 A | 3/1993 | Schulman et al. | |
| 5,234,692 A | 8/1993 | Magruder et al. | |
| 5,234,693 A | 8/1993 | Magruder et al. | |
| 5,292,344 A | 3/1994 | Douglas | |
| 5,312,439 A | 5/1994 | Loeb | |
| 5,501,703 A | 3/1996 | Holsheimer | |
| 5,728,396 A | 3/1998 | Peery et al. | |
| 5,938,688 A | 8/1999 | Schiff | |
| 6,016,449 A | 1/2000 | Fischell et al. | |
| 6,044,304 A * | 3/2000 | Baudino | 607/116 |
| 6,219,580 B1 | 4/2001 | Faltys et al. | |
| 6,272,382 B1 | 8/2001 | Faltys et al. | |
| 6,308,101 B1 | 10/2001 | Faltys et al. | |
| 6,368,315 B1 | 4/2002 | Gillis et al. | |
| 6,381,496 B1 | 4/2002 | Meadows et al. | |
| 6,487,446 B1 | 11/2002 | Hill et al. | |
| 6,516,227 B1 | 2/2003 | Meadows et al. | |
| 6,539,263 B1 | 3/2003 | Schiff et al. | |
| 6,553,263 B1 | 4/2003 | Meadows et al. | |
| 6,620,151 B2 | 9/2003 | Blischak et al. | |
| 6,666,845 B2 | 12/2003 | Hooper et al. | |
| 6,735,475 B1 | 5/2004 | Whitehurst et al. | |
| 6,740,072 B2 | 5/2004 | Starkweather et al. | |
| 6,741,892 B1 | 5/2004 | Meadows et al. | |
| 6,760,626 B1 | 7/2004 | Boveja | |
| 6,770,067 B2 | 8/2004 | Lorenzen et al. | |
| 6,840,919 B1 * | 1/2005 | Håkansson | 604/175 |
| 6,920,359 B2 | 7/2005 | Meadows et al. | |
| 7,013,177 B1 | 3/2006 | Whitehurst et al. | |
| 2005/0055064 A1 | 3/2005 | Meadows et al. | |
| 2005/0107842 A1 * | 5/2005 | Rezai | 607/50 |
| 2006/0122664 A1 * | 6/2006 | Sacha et al. | 607/57 |
| 2007/0100393 A1 * | 5/2007 | Whitehurst et al. | 607/45 |

OTHER PUBLICATIONS

U.S. Appl. No. 11/030,546, filed Jan. 5, 2004, Meadows, Devices and Methods for Brain Stimulation.

U.S. Appl. No. 11/230,052, filed Sep. 19, 2005; Meadows, Devices and Methods Using an Implantable Pulse Generator for Brain Stimulation.

U.S. Appl. No. 11/241,156, filed Sep. 30, 2005, Moffitt et al., Devices with Cannula and Electrode Lead for Brain Stimulation and Methods of Use and Manufacture.

* cited by examiner

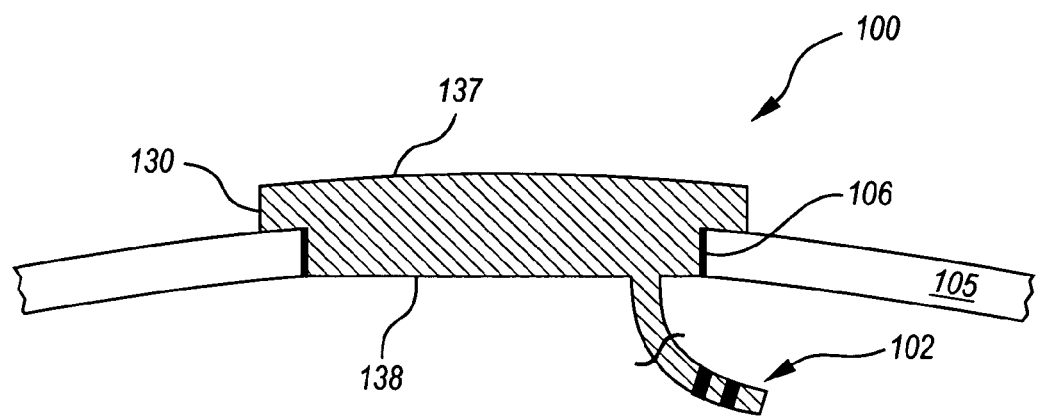
Fig. 7
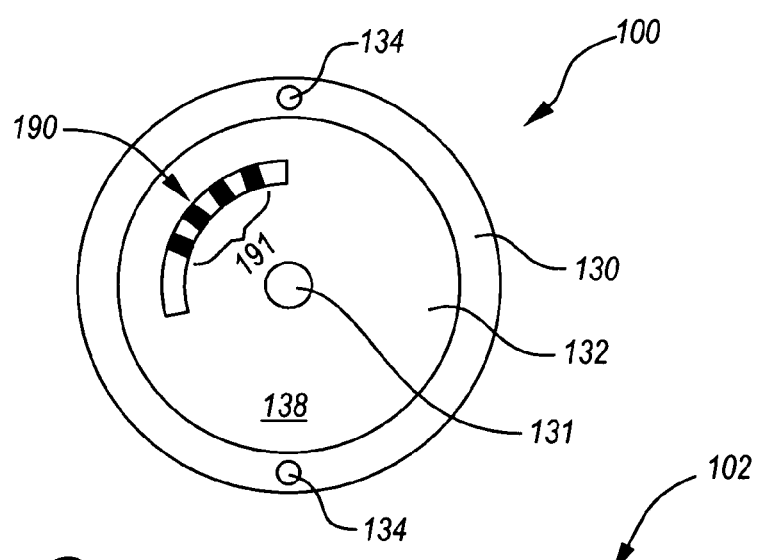
Fig. 8
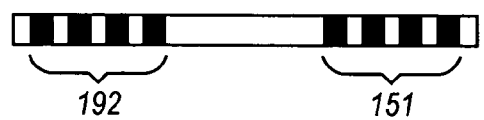

CRANIALLY MOUNTED STIMULATION SYSTEMS AND METHODS

BACKGROUND

Deep brain stimulation (DBS) and other related procedures involving the implantation of leads and catheters in the brain are increasingly used to treat such conditions as Parkinson's disease, dystonia, essential tremor, seizure disorders, obesity, depression, motor control disorders, and other debilitating diseases. During these procedures, a catheter, lead, or other medical device is strategically placed at a target site in the brain.

Microelectrode recording is generally performed with a microelectrode recording (MER) system. The MER system includes a small diameter electrode with a relatively small surface area optimal for recording single cell activity. The microelectrode may essentially be an insulated wire that has at least the distal portion uninsulated to receive electrical signals. The microelectrode functions as a probe to locate an optimal site in the brain for deep brain stimulation. Activity detected through the microelectrode is recorded by the MER system.

After an optimal site in the brain for deep brain stimulation has been identified by the microelectrode recording, a macroelectrode is typically used to test whether the applied stimulation has the intended therapeutic effect. Once macrostimulation confirms that stimulation at the optimal site provides the intended therapeutic effect, the macroelectrode is withdrawn from the brain and a DBS lead is permanently implanted at the optimal site in the brain for deep brain stimulation.

The DBS lead may then be connected to a stimulation device, such as an implantable pulse generator (IPG) or other type of stimulator. The stimulation device is configured to generate the electrical current that is applied to the stimulation site within the brain. However, the stimulation device is often located at a site that is relatively distant from the stimulation site. For example, the stimulation device may be mounted under the skin of the chest. Hence, in many applications, the DBS lead must exit the skull or cranium, make a right-angle bend at the outer surface of the cranium, and then be routed to the location of the stimulation device. The extracranial portion of the DBS lead and the tight right angle bend present severe stress exposure for the lead and may result in the breakage of the lead, and thus premature explantation of the lead.

SUMMARY

An exemplary system includes a stimulator with a hollow lumen extending therethrough and configured to be at least partially disposed within a burr hole in a cranium of a patient, a stimulating member configured to apply a stimulus to a stimulation site within the patient, and coupling member configured to extend at least partially through the lumen and couple the stimulating member to the stimulator.

Exemplary methods of applying at least one stimulus to a stimulation site within a patient include implanting a lead with a number of electrodes disposed thereon within a cavity formed by a cranium, implanting a stimulator such that the stimulator is at least partially disposed within a burr hole in the cranium, removably coupling the lead to the stimulator, and applying the at least one stimulus to a stimulation site within the cavity formed by the cranium via one or more of the electrodes.

BRIEF DESCRIPTION OF THE DRAWINGS

The accompanying drawings illustrate various embodiments of the present systems and methods and are a part of the specification. The illustrated embodiments are merely examples of the present systems and methods and do not limit the scope of the invention.

FIG. 7 is a cross sectional side view of the stimulator with the lead coupled directly to the bottom surface of the stimulator according to principles described herein.

FIG. 8 is a bottom view of an exemplary stimulator configured to couple directly to the lead according to principles described herein.

Throughout the drawings, identical reference numbers designate similar, but not necessarily identical, elements.

DETAILED DESCRIPTION

Figure 1:
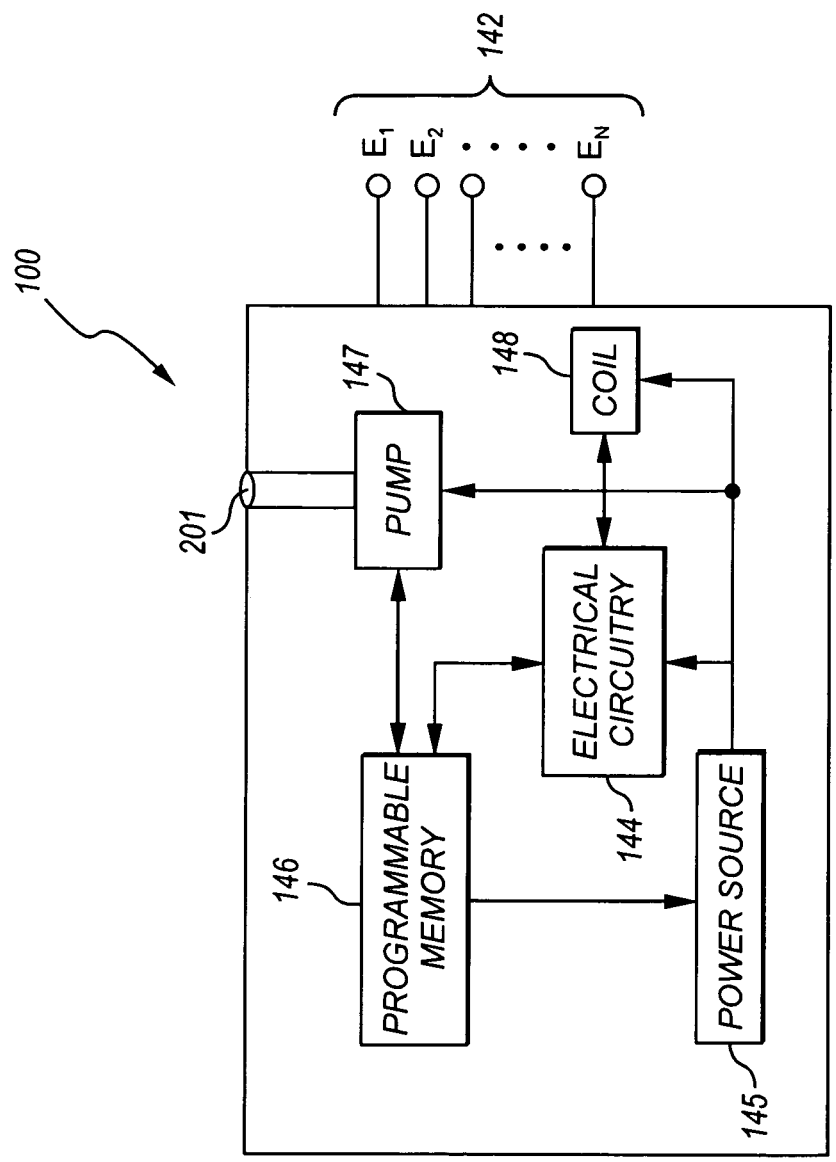
FIG. 1 is a block diagram illustrating a number of components of an exemplary stimulator according to principles described herein.

A number of exemplary cranially mounted stimulation systems are described herein. In some examples, a stimulator is at least partially disposed within a burr hole in a cranium of a patient. A stimulating member, such as a lead or a catheter, is coupled to and extends from the stimulator. The stimulating member is configured to apply a stimulus to a stimulation site within the patient and is entirely disposed within the patient.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment.

The appearance of the phrase "in one embodiment" in various places in the specification are not necessarily all referring to the same embodiment.

As used herein and in the appended claims, the term "stimulator" will be used broadly to refer to any type of device that is configured to deliver a stimulus to a stimulation site within a patient. For example, the stimulator may include an implantable pulse generator (IPG) coupled to one or more leads having a number of electrodes, a spinal cord stimulator (SCS), a cochlear implant, a deep brain stimulator, a drug pump, a micro-drug pump, or any other type of stimulator configured to deliver a stimulus to a stimulation site within a patient. Exemplary IPGs suitable for use as described herein include, but are not necessarily limited to, those disclosed in U.S. Pat. Nos. 6,381,496; 6,553,263; and 6,760,626. Exemplary spinal cord stimulators suitable for use as described herein include, but are not necessarily limited to, those disclosed in U.S. Pat. Nos. 5,501,703; 6,487,446; and 6,516,227. Exemplary cochlear implants suitable for use as described herein include, but are not necessarily limited to, those disclosed in U.S. Pat. Nos. 6,219,580; 6,272,382; and 6,308,101. Exemplary deep brain stimulators suitable for use as described herein include, but are not necessarily limited to, those disclosed in U.S. Pat. Nos. 5,938,688; 6,016,449; and 6,539,263. All of these listed patents are incorporated herein by reference in their respective entireties.

As used herein and in the appended claims, unless otherwise specifically denoted, the term "stimulation site" will be used to refer to any nerve, muscle, organ, or other tissue within a patient that is stimulated by a stimulator. For example, in the case of deep brain stimulation, the stimulation site may be, but is not limited to, any nerve or tissue within the brain.

The stimulus applied to the stimulation site may include electrical stimulation, which is a type of neuromodulation. Electrical stimulation will be described in more detail below. The stimulus may additionally or alternatively include drug stimulation, which is another type of neuromodulation. For example, therapeutic dosages of one or more drugs may be infused into the stimulation site to treat any of a wide variety of medical conditions. Additionally or alternatively, the stimulus applied to the stimulation site may include any other suitable stimulus such as, but not limited to, chemical stimulation, thermal stimulation, electromagnetic stimulation, and/or mechanical stimulation. Consequently, the terms "stimulus" and "stimulation" will be used interchangeably herein and in the appended claims, unless otherwise specifically denoted, to refer to electrical stimulation, drug stimulation, chemical stimulation, thermal stimulation, electromagnetic stimulation, mechanical stimulation, and/or any other suitable stimulation.

Turning to the drawings, FIG. 1 is a block diagram illustrating a number of components of an exemplary stimulator (100). As shown in FIG. 1, the stimulator (100) may include a power source (145), a programmable memory (146), electrical circuitry (144), a pump (147), and a coil (148). It will be recognized that the stimulator (100) may include additional and/or alternative components as best serves a particular application.

The power source (145) is configured to output a voltage used to supply the various components within the stimulator (100) with power and/or to generate the power used for electrical stimulation. In some examples, the power source (145) may be recharged using an external recharging device. Alternatively, the stimulator (100) may include one or more components configured to receive power from a device that is implanted within the patient.

The stimulator (100) may also include a coil (148) configured to receive and/or emit a magnetic field (also referred to as a radio frequency (RF) field) that is used to communicate with or receive power from one or more external devices that support the implanted stimulator (100), examples of which will be described below. Such communication and/or power transfer may include, but is not limited to, transcutaneously receiving data from the external device, transmitting data to the external device, and/or receiving power used to recharge the power source (145).

The stimulator (100) may also include electrical circuitry (144) configured to produce electrical stimulation pulses that are delivered to the stimulation site via a number of electrodes (142). In some embodiments, as will be described in more detail below, the stimulator (100) may be configured to produce monopolar stimulation. The stimulator (100) may alternatively or additionally be configured to produce multipolar stimulation including, but not limited to, bipolar or tripolar stimulation.

The electrical circuitry (144) may include one or more processors configured to decode stimulation parameters and generate the corresponding stimulation pulses. In some embodiments, the stimulator (100) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (100) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the stimulator (100) to adjust the stimulation parameters such that the stimulation applied by the stimulator (100) is safe and efficacious for a particular medical condition and/or for a particular patient. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, electrode configuration (i.e., anode-cathode assignment), burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused into the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on neural or other tissue. Thus, in some embodiments, the stimulation parameters may be adjusted by the patient, a clinician, or other user of the stimulator (100) as best serves a particular stimulation site. For example, the amplitude of the stimulation current applied to a stimulation site may be adjusted to have a relatively low value to target a nerve having relatively large diameter fibers. The stimulator (100) may also, or alternatively, increase excitement of a stimulation site by applying a stimulation current having a relatively low frequency to the stimulation site (e.g., less than 100 Hz). The stimulator (100) may also or alternatively decrease excitement of a stimulation site by applying a relatively high frequency to the stimulation site (e.g., greater than 100 Hz). The stimulator (100) may additionally or alternatively be programmed to apply the stimulation current to a stimulation site intermittently or continuously.

In some examples, the stimulation parameters may also be automatically adjusted by the stimulator (100). For example, the amplitude of the stimulation current applied to a stimulation site may be adjusted by running different programs at different times of the day, corresponding to sleep and wake operation, or it may be changed in response to a secondary controller which might determine that the posture of the patient had changed.

As shown in FIG. 1, the stimulator (100) may be coupled to a number of electrodes or electrode contacts $E_1$-$E_n$ (142) configured to apply the electrical stimulation current to the stimulation site. As shown in FIG. 1, there may be any number of electrodes (142) as best serves a particular application. In some examples, one or more of the electrodes (142) may be designated as stimulating electrodes and one of the electrodes (142) may be designated as an indifferent electrode used to complete one or more stimulation circuits. In some examples, as will be described in more detail below, the electrodes (142) may be a part of a lead that is coupled to the body of the stimulator (100).

Additionally, the exemplary stimulator (100) shown in FIG. 1 may be configured to provide drug stimulation to a patient by applying one or more drugs to a stimulation site. For this purpose, the stimulator (100) includes a pump (147) and one or more infusion outlets (201). The pump (147) is configured to store and dispense the one or more drugs, for example, through the infusion outlet (201). The infusion outlet (201) facilitates the infusion of one or more drugs into the stimulation site. The infusion outlet (201) may dispense one or more drugs directly to the stimulation site. Alternatively, one or more catheters may be coupled to the infusion outlet (201) to deliver the drug therapy to a stimulation site some distance from the body of the stimulator (100).

The pump (147) or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

The one or more drugs that may be applied to a stimulation site may have an excitatory effect on the stimulation site. Additionally or alternatively, the one or more drugs may have an inhibitory effect on the stimulation site. Exemplary excitatory drugs that may be applied to a stimulation site include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clondine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site include at least one or more of the following substances: non-steroidal anti-inflammatory medications (NSAIDS) (e.g., ibuprofen, naproxen, VIOXX); estrogens (e.g., estrone, estradiol, estriol, esters of estradiol, synthetic estrogens such as diethylstilbestrol, quinestrol, chlorotrianisene); progestins (e.g., naturally occurring progesterone, medroxyprogesterone acetate, norethindrone acetate, hydroxyprogesterone acetate, norgestrel, norethindrone); antiestrogens (e.g., clomiphene, tamoxifen); gonadotropin releasing hormone agonist analogues (e.g., leuprolide acetate, nafarelin); androgens (e.g., testosterone, testosterone cypionate, fluoxymesterone, fluoxymesterone, danazol, testolactone); antiandrogens (e.g., cyproterone acetate, flutamide); opiods (e.g., morphine); ziconitide; and/or antidepressents (e.g., serotonin specific reuptake inhibitors and tricyclic antidepressants).

Any of the above listed drugs, alone or in combination, or other drugs developed or shown effective to treat a medical condition or its symptoms may be applied to the stimulation site. In some embodiments, the one or more drugs are infused chronically into the stimulation site. Additionally or alternatively, the one or more drugs may be infused acutely into the stimulation site in response to a biological signal or a sensed need for the one or more drugs.

As mentioned, the stimulator (100) of FIG. 1 may be used to perform deep brain stimulation or any other type of stimulation. In many examples, as described above, the stimulator (100) is coupled to one or more leads and/or catheters that are implanted within the brain. However, because the stimulator (100) is often located at a site that is relatively distant from the brain, the leads typically have to exit the cranium, make a right-angle bend at the outer surface of the cranium, and then be routed to the stimulator (100).

Figure 2:
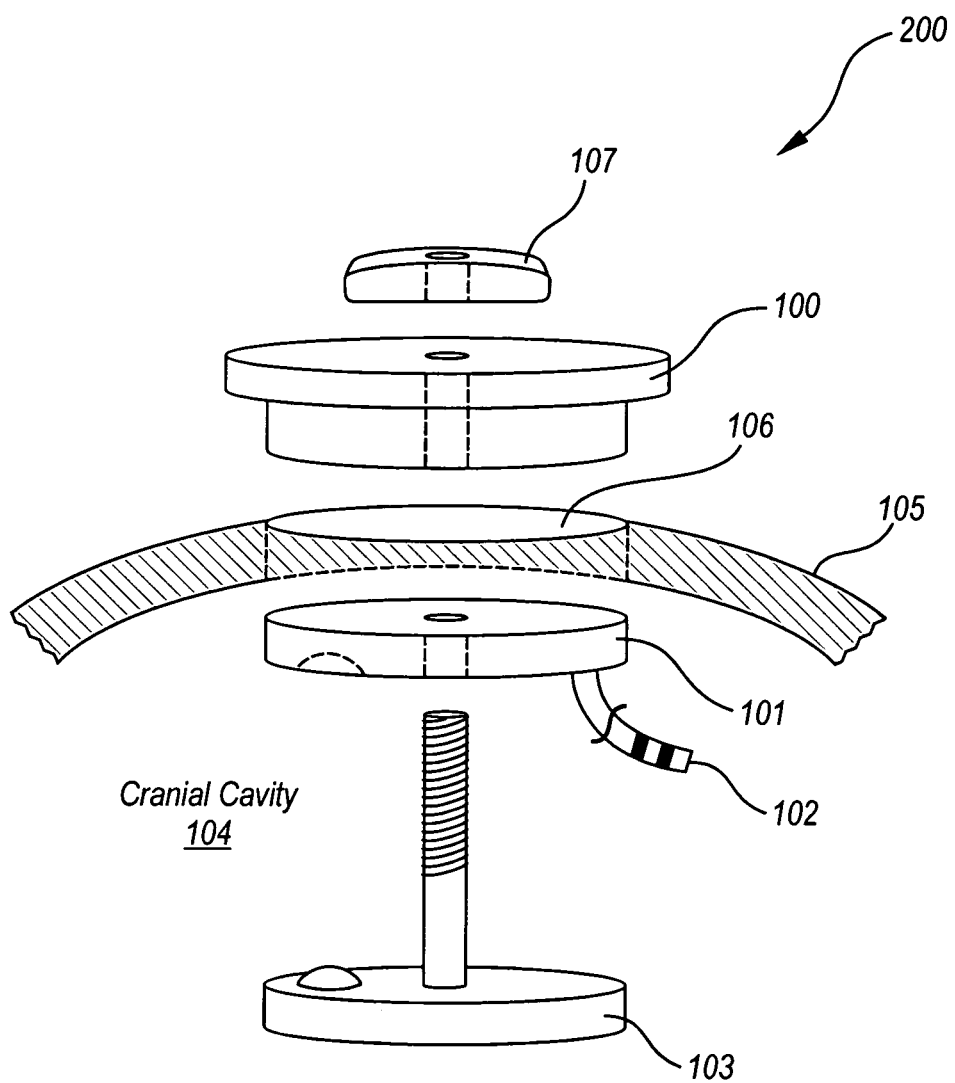
FIG. 2 shows an exploded perspective view of an exemplary cranially mounted deep brain stimulation (DBS) system according to principles described herein.

FIG. 2 shows an exploded perspective view of an exemplary cranially mounted DBS system (200). The cranially mounted DBS system (200) of FIG. 2 is configured such that the DBS leads and/or catheters that are coupled to the stimulator (100) do not have to exit the cranium. As shown in FIG. 2, the system (200) includes a stimulator (100), a lead connector (101), a lead (102), a T-bolt (103), and a securing nut (107). Each of these components will be described in more detail below. It will be recognized that the system (200) may additionally or alternatively include one or more catheters and/or multiple leads.

FIG. 2 shows that a burr hole (106) may be surgically drilled through the cranium (105). The burr hole (106) may be of any suitable size or shape. In some examples, as shown in FIG. 2, the burr hole (106) is circular. As will be described in more detail below, the stimulator (100) is configured to be at least partially mounted within the burr hole (106). The T-bolt (103) and nut (107) are configured to secure the lead connector (101) to the bottom surface of the stimulator (100). Hence, the lead (102) may be positioned within the cranial cavity or brain (104) without having to pass through the cranium (105).

Figure 3A:
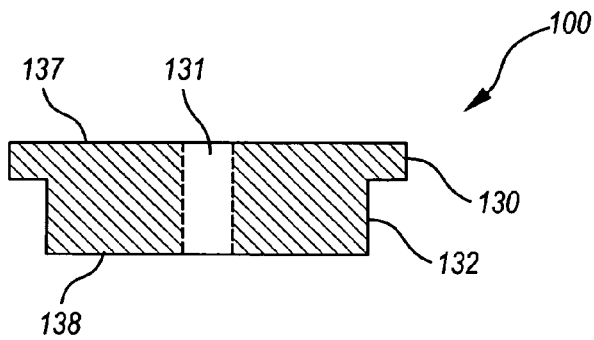
FIG. 3A is a cross sectional side view of an exemplary stimulator according to principles described herein.

An exemplary structure of the stimulator (100) will be described in connection with FIGS. 3A-3C. FIG. 3A is a cross sectional side view of the stimulator (100). As shown in FIG. 3A, the stimulator (100) includes a main housing or casing (132), a lip member (130), and a central lumen (131). The perimeter of the main housing (132) is substantially equal to or less than the perimeter of the burr hole (106; FIG. 2) so that the main housing (132) of the stimulator (100) may fit within the burr hole (106; FIG. 2).

The lip member (130) has a perimeter that is larger than the perimeter of the burr hole (106; FIG. 2) to prevent the stimulator (100) from falling through the burr hole (106; FIG. 2) into the cranial cavity (104; FIG. 2). The lip member (130) may have any suitable thickness.

One or more components housed within the stimulator (100) may be located within the lip member (130). However, in some alternative embodiments, all of the components of the stimulator (100) are located within the main housing (132).

The central lumen (131), as shown in FIG. 3A, extends from the top surface (137) of the lip member (130) to the bottom surface (138) of the stimulator (100). As will be described in more detail, the T-bolt (103; FIG. 2) is configured to extend through the central lumen (131) to attach the lead connector (101; FIG. 2) to the stimulator (100).

Figure 3B:
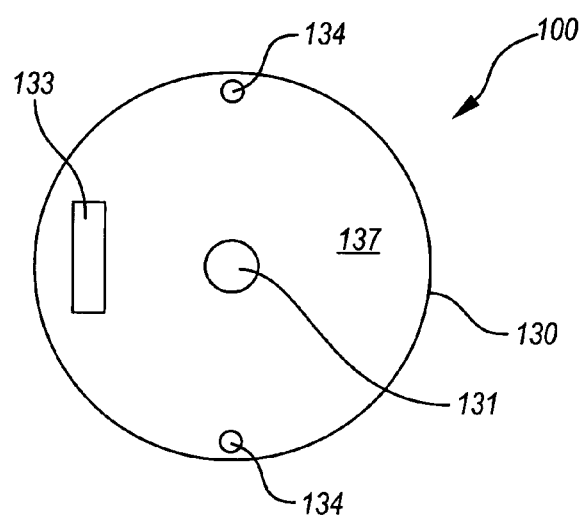
FIG. 3B is a top view of the stimulator of FIG. 3A according to principles described herein.

FIG. 3B is a top view of the stimulator (100) of FIG. 3A, looking down on the lip member (130). The central lumen (131) and one or more holes (134) may be seen in FIG. 3B. The one or more holes (134) may be located towards the outer edge of the lip member (130) and are used to couple a spanner wrench or other rotation driving device to the stimulator (100). The spanner wrench may be used to rotate the stimulator (100) to a desired position within the burr hole (106; FIG. 2).

FIG. 3B also shows that a communication port (133) may additionally be included on the top surface (137) of the lip member (130). The communication port (133) may be used by an external device to communicate with and/or transfer power to the stimulator (100). Any other communication and/or electronic circuitry may additionally or alternatively be included on the top surface (137) of the lip member (130) or elsewhere within the stimulator (100).

Figure 3C:
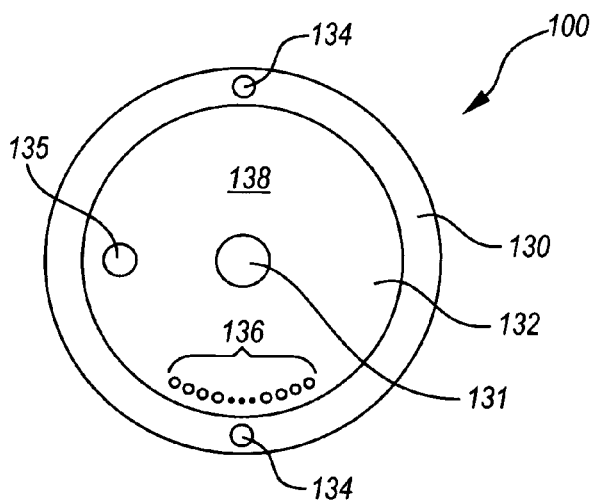
FIG. 3C is a bottom view of the stimulator of FIG. 3A according to principles described herein.

FIG. 3C is a bottom view of the stimulator (100) of FIG. 3A and shows the lip member (130) in the background, and the bottom surface (138) of the main housing (132) in the foreground. The holes (134) for the spanner wrench and the central lumen (131) are also shown. FIG. 3C also shows a registration depression (135) that may be used to align the stimulator (100) with the lead connector (101; FIG. 2), as will be described in more detail below. It will be recognized that the stimulator (100) may additionally or alternatively include any other device or structure configured to align the stimulator (100) with the lead connector (101; FIG. 2). For example, the stimulator (100) may additionally or alternatively include a registration protrusion, a pin, a hole, an adhesive, a groove, or any other device or structure configured to align the stimulator (100) with the lead connector (101; FIG. 2).

A number of feedthrough electrical contacts (136) may also be located on the bottom surface (138) of the stimulator (100). As will be explained in more detail below, the feedthrough electrical contacts (136) may be aligned with corresponding electrical contacts on the top surface of the lead connector (101; FIG. 2). In some examples, one or more of the feedthrough electrical contacts (136) are flush with the bottom surface (138) of the stimulator (100). Additionally or alternatively, one or more of the feedthrough electrical contacts (136) may be raised or depressed relative to the bottom surface (138) of the stimulator (136). Corresponding raised or depressed contacts will be provided on the lead connector (101; FIG. 2) to electrically couple the lead connector (101; FIG. 2) with the electronics of the stimulator (100). The feedthrough electrical contacts (136) may be positioned at any location on the bottom surface (138) of the stimulator (100) as best serves a particular application.

Figure 4A:
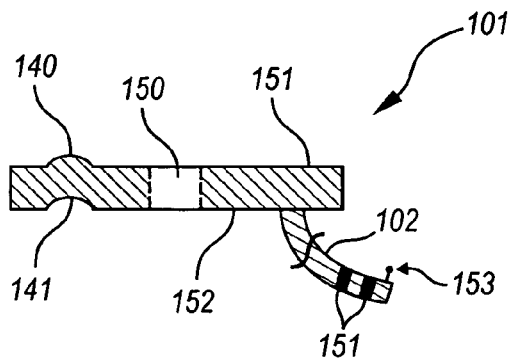
FIG. 4A is a cross sectional side view of an exemplary lead connector according to principles described herein.
Figure 4B:
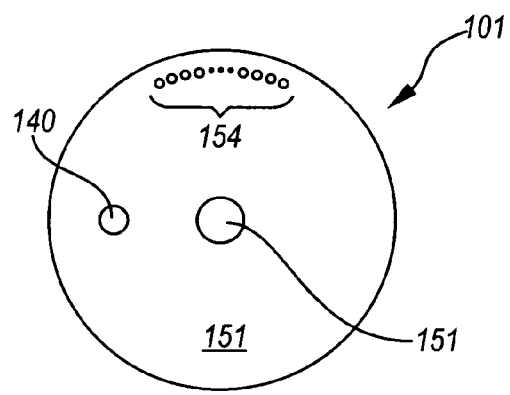
FIG. 4B is a top view of the lead connector of FIG. 4A according to principles described herein.
Figure 4C:
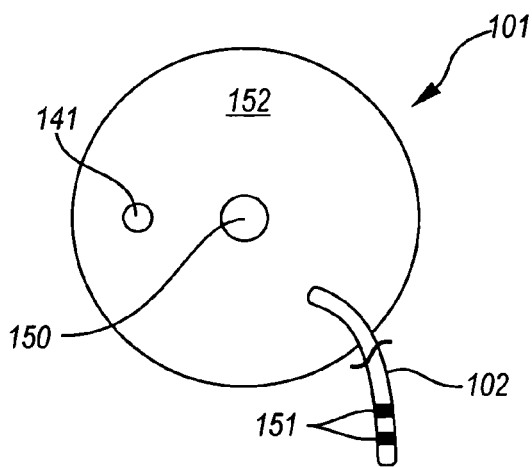
FIG. 4C is a bottom view of the lead connector of FIG. 4A according to principles described herein.

Turning to FIGS. 4A-4C, the lead connector (101) will now be described in more detail. FIG. 4A is a cross sectional side view of the lead connector (101). The lead connector (101) may be made out of any suitable material. For example, the lead connector (101) may be made out of a compliant or semi-compliant material so as to allow compression by the T-bolt (103; FIG. 2) against the bottom surface (138; FIG. 3A) of the stimulator (100; FIG. 3A.) The material may be silicon rubber, plastic, metal, ceramic, or any other suitable material or combination of materials.

As shown in the example of FIG. 4A, the lead connector (101) includes a central lumen (150), a registration protrusion (140), and a registration depression (141). The central lumen (150) extends from the top surface (151) of the lead connector (101) through to the bottom surface (152) of the lead connector (101). As will be described in more detail, the T-bolt (103; FIG. 2) is configured to extend through the central lumen (150).

The registration protrusion (140) shown in FIG. 4A is located on the top surface (151) of the lead connector (101) and is configured to couple with the registration depression (135; FIG. 3C) on the bottom surface (138; FIG. 3C) of the stimulator (100; FIG. 3C). In this manner, the lead connector (100) may be properly aligned in a desired orientation with respect to the stimulator (100; FIG. 3C). It will be recognized that the lead connector (101) may additionally or alternatively include any other device or structure configured to align the lead connector (101) in a particular orientation with respect to the stimulator (100). For example, the lead connector (101) may additionally or alternatively include a registration depression, a pin, a hole, an adhesive, a groove, or any other device or structure configured to align the lead connector (101) with the stimulator (100).

As shown in FIG. 4A, the lead connector (101) may additionally or alternatively include a registration depression (141) located on the bottom surface (152) of the lead connector (101). The registration depression (141), as will be described in more detail below, may be used to align the lead connector (101) in a desired orientation with respect to the T-bolt (103; FIG. 1). It will be recognized that the lead connector (101) may additionally or alternatively include any other device or structure configured to align the lead connector (101) with the T-bolt (103; FIG. 2). For example, the lead connector (101) may additionally or alternatively include a registration protrusion, a pin, a hole, an adhesive, a groove, or any other device or structure configured to align the lead connector (101) with the T-bolt (103; FIG. 2).

FIG. 4A also shows that a proximal end of the lead (102) is coupled to the lead connector (101). It will be recognized that any number of leads (102) may be coupled to the lead connector (101). In some examples, as shown in FIG. 4A, the lead (102) is coupled to the bottom surface (152) of the lead connector (101). However, it will be recognized that the lead (102) may be coupled to any portion of the lead connector (101) as best serves a particular application. One or more catheters (not shown) may additionally or alternatively be coupled to the lead connector (101).

As shown in FIG. 4A, the lead (102) may include a number of electrical contacts (151). The number of contacts (151) included on the lead (102) may vary as best serves a particular application. These electrical contacts (151) may be selectively configured to serve as recording electrodes and/or stimulating electrodes. For example, one or more of the electrical contacts (151) may be configured to serve as recording electrodes. The lead (102) may then be coupled to a recording device and used to find an optimal site in the brain for deep brain stimulation with those contacts configured as recording electrodes cooperating with the recording device. Once the optimal stimulation site has been determined, one or more of the contacts (151) configured to serve as stimulating electrodes are used by the stimulator (100) to apply deep brain stimulation to the stimulation site. This dual functionality of the lead (102) (i.e., the ability to serve as a recording lead and a stimulating lead) allows the lead (102) to remain permanently in the brain during the recording and stimulating procedures. It will be recognized that the lead (102) may alternatively only include recording electrodes or only stimulating electrodes.

The lead (102) may have any length as best serves a particular application. Moreover, in some examples, the lead (102) may include an offset portion (153) configured to engage with a stylet or other guiding device. The stylet, when coupled to the offset portion (153), may be used to guide the lead to a stimulation site within the brain. The stylet may alternatively be inserted through the central lumen (150) of the lead connector (101) or through a central lumen of the lead (102). Alternatively, the stylet may be inserted into the brain through a separate burr hole. The offset portion (153) may be positioned at any location along the lead (102) and may be made out of any suitable material. In some examples, the lead (102) does not include the offset portion (153).

FIG. 4B is a top view of the lead connector (101) of FIG. 4A. As shown in FIG. 4B, the lead connector (101) may be in the shape of a disc. However, it will be recognized that the lead connector (101) may have any other suitable shape, including, but not limited to, an oval, elliptical or rectangular shape. The registration protrusion (140) and the central lumen (150) are shown on the top surface (151) of the lead connector (101).

FIG. 4B also shows that a number of electrical contacts (154) may also be located on the top surface (151) of the lead connector (101). Each of the electrical contacts (154) is electrically coupled to one of the electrical contacts (151; FIG. 4A) located on the lead (102; FIG. 4A).

As will be explained in more detail below, the electrical contacts (154) may be aligned to make physical contact with the feedthrough electrical contacts (136; FIG. 3C) on the stimulator (100; FIG. 3C). In some examples, one or more of the electrical contacts (154) are flush with the top surface (151) of the lead connector (101). Additionally or alternatively, one or more of the electrical contacts (154) may be raised or depressed to correspond to the contacts (136; FIG. 3C) on the stimulator (100; FIG. 3C), as mentioned above. The electrical contacts (154) may be positioned at any location on the top surface (151) of the lead connector (101) as best serves a particular application.

FIG. 4C is a bottom view of the lead connector (101) of FIG. 4A. FIG. 4C shows the registration depression (141), central lumen (150), and lead (102). The registration depression (141) and lead (102) may be located at any location on the bottom surface (152) of the lead connector (101) as best serves a particular application.

Figure 5A:
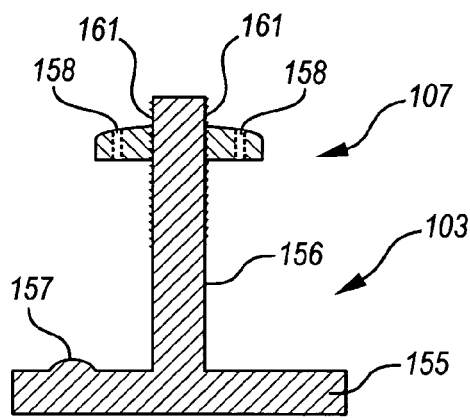
FIG. 5A is a cross sectional side view of the T-bolt and nut according to principles described herein.

The T-bolt (103) and the nut (107) will now be described in connection with FIGS. 5A-5C. FIG. 5A is a cross sectional side view of the T-bolt (103) and nut (107). As shown in FIG. 5A, the T-bolt (103) includes a base member (155) and a shaft member (156). The base member (155) and the shaft member (156) form the shape of a "T", as shown in FIG. 5A. As will be described in more detail below, the shaft (156) may be inserted through the central lumens of the lead connector (101; FIG. 2) and stimulator (100; FIG. 2). The nut (107) may then be threaded onto the shaft (156) to secure the lead connector (101; FIG. 2) to the stimulator (100; FIG. 2).

The shaft (156) may have any suitable length and shape as best serves a particular application. For example, the shaft (156) may have, but is not limited to, a circular or rectangular cross-section. As shown in FIG. 5A, the shaft (156) may include threads (161) configured to match corresponding threads on the inside of the nut (107). The nut (107) may be coupled to the shaft (156) in any suitable manner including, but not limited to, threading the nut (107) onto the shaft (156).

FIG. 5A shows that the base member (155) may include a registration protrusion (157). The registration protrusion (157) may be used to align the T-bolt (103) with the lead connector (101; FIG. 2). It will be recognized that the base member (155) of the T-bolt (103) may additionally or alternatively include any other device or structure configured to align the T-bolt (103) in a particular orientation with respect to the lead connector (101; FIG. 2). For example, the T-bolt (103) may additionally or alternatively include a registration depression, a pin, a hole, an adhesive, a groove, or any other device or structure configured to align the T-bolt (103) with the lead connector (101; FIG. 2).

The nut (107), as mentioned above, may be used to secure the lead connector (101; FIG. 2) to the stimulator (100; FIG. 2). The nut (107) may be dome-shaped, as shown in FIG. 5A, or it may have any other shape or structure as best serves a particular application. The nut (107) may include one or more holes (158) that are used to couple a spanner wrench or other rotation driving device to the nut (107). The spanner wrench may be used to tighten the nut (107) against the stimulator (100).

It will be recognized that any coupling device other than, or in addition to, the T-bolt (103) may be used to couple the lead connector (101; FIG. 2) to the stimulator (100; FIG. 2). Furthermore, any fastening device other than, or in addition to, the nut (107) may be used to secure the lead connector (101; FIG. 2) to the stimulator (100; FIG. 2). For example, one or more clamps, rivets, and/or other fastening devices may be used to secure the lead connector (101; FIG. 2) to the stimulator (100; FIG. 2). In some cases, only a coupling device or a fastening device will be needed.

Figure 5B:
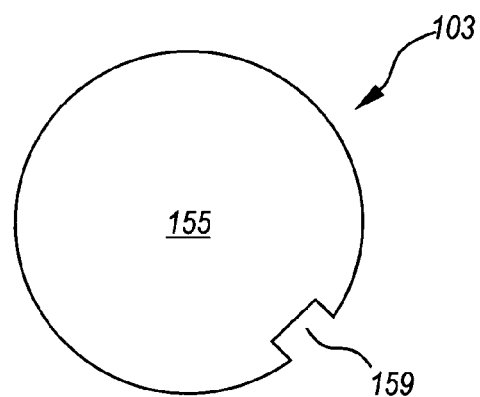
FIG. 5B is a bottom view of the base member of the T-bolt of FIG. 5A according to principles described herein.

FIG. 5B is a bottom view of the base member (155) of the T-bolt (103) of FIG. 5A. As shown in FIG. 5B, the base member (155) may be substantially disc-shaped. However, it will be recognized that the base member (155) may have any other suitable shape as best serves a particular as best serves a particular application. The base member (155) may include a notch (159) or other relief through which the lead (102; FIG. 2) may extend.

Figure 5C:
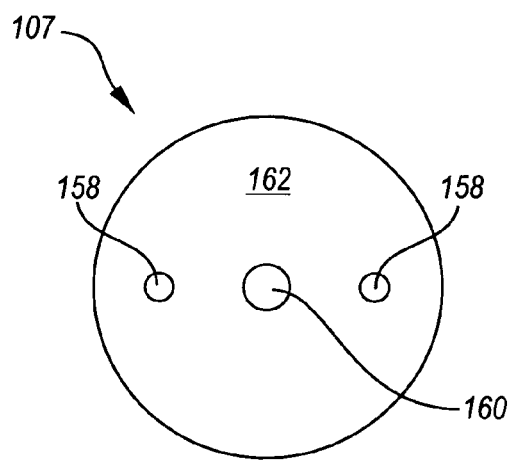
FIG. 5C is a top view of the nut of FIG. 5A according to principles described herein.

FIG. 5C is a top view of the nut (107) of FIG. 5A. FIG. 5C shows that the holes (158) and the central lumen (160) communicate with the top surface (162) of the nut (107). The nut (107) may have a circular perimeter, as shown in FIG. 5C. However, it will be recognized that perimeter of the nut (107) may alternatively have any other suitable shape as best serves a particular application.

Figure 6:
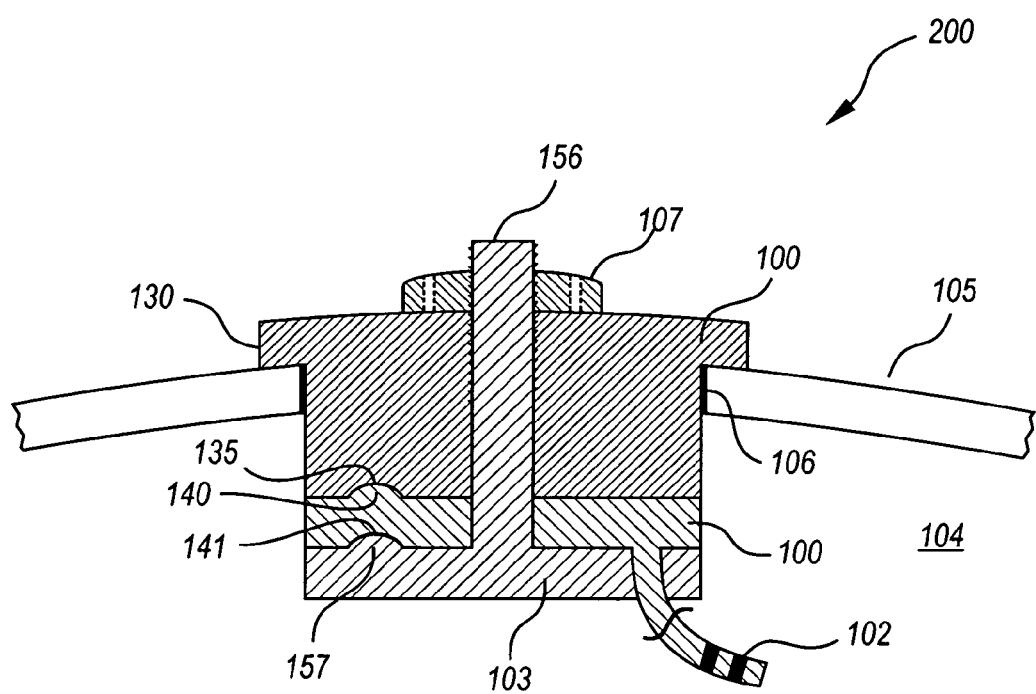
FIG. 6 is a cross sectional side view of the exemplary cranially mounted DBS system of FIG. 2 according to principles described herein.

FIG. 6 is a cross sectional side view of the exemplary cranially-mounted DBS system (200). As shown in FIG. 6, the stimulator (100) is placed in the burr hole (106) that extends through the cranium (105). The lip member (130) of the stimulator (100) rests on a portion of the cranium (105) surrounding the burr hole (106) and thus prevents the stimulator (100) from falling into the cranial cavity (104).

FIG. 6 shows that the stimulator (100) is coupled to the lead connector (101) using the T-bolt (103) and nut (107). By tightening the nut (107), the top surface of the lead connector (101) is pressed against the bottom surface of the stimulator (100). The electrical contacts (154; FIG. 4B) of the lead connector (101) then make physical contact with the electrical contacts (136; FIG. 3C) of the stimulator (100). The connection may be made hermetic by applying continuous and sufficient pressure with the T-bolt (103) and nut (107).

The stimulator (100) and lead connector (101) are aligned by aligning the registration depression (135) of the stimulator (100) with the registration protrusion (140) of the lead connector (101). The T-bolt (103) and the lead connector (101) are aligned by aligning the registration depression (141) of the lead connector (101) with the registration protrusion (157) of the T-bolt (103). This alignment of the various components serves to align the electrical contacts on the various components thus providing an electrical connection from the stimulator (100), through the lead connector (101) to the electrodes of the lead (102). This alignment of the various components described also serves to position the lead (102) through or past the base member (155) of the T-bolt (103).

Although FIG. 6 shows the lead connector (101) coupled to the stimulator (100), it will be recognized that the lead connector (101) may alternatively be coupled to any other device. For example, the nut (107) may be removed from the T-bolt (103) and the stimulator (100) may be removed from the burr hole (106). A different device, such as a recording device, may then be coupled to the lead connector (101). Hence, the same lead (102) may be used with multiple devices for different purposes without having to be removed from the brain.

In some examples, the lead (102) may be coupled directly to the stimulator (100). For example, FIG. 7 is a cross sectional side view of the stimulator (100) with the lead (102) coupled directly to the bottom surface (138) of the stimulator (100). In some examples, the lead (102) is permanently coupled to the stimulator (100).

As shown in FIG. 7, the stimulator (100) is implanted within a burr hole (106) that has been drilled into the cranium (105). The cranially mounted deep brain stimulation system of FIG. 7 uses fewer components and occupies less volume than the cranially mounted deep brain stimulation of FIG. 6, which may be advantageous in some applications. Furthermore, the stimulator (100) shown in FIG. 7 does not have a central lumen, which may also be advantageous in some applications.

Alternatively, the lead (102) may be coupled directly to the stimulator (100) with the T-bolt (103; FIG. 2) and nut (107; FIG. 2) so as to avoid the use of the lead connector (101; FIG. 2). FIG. 8 is a bottom view of an exemplary stimulator (100) configured to couple directly to the lead (102). As shown in FIG. 8, the bottom surface (138) may include an array (190) of electrical contacts (191). The array (190) may be flush with the bottom surface (138). Alternatively, the array (190) may be raised or depressed. The electrical contacts (191) are spaced such that they align with a number of electrical contacts (192) that are disposed on the lead (102). The T-bolt (103; FIG. 2) and nut (107; FIG. 2) may then be used to press the lead (102) against the bottom surface (138) of the stimulator (100) such that the electrical contacts (191) located on the bottom surface (138) of the stimulator (100) are electrically coupled to the electrode contacts (192) located on the lead (102).

Figure 9A:
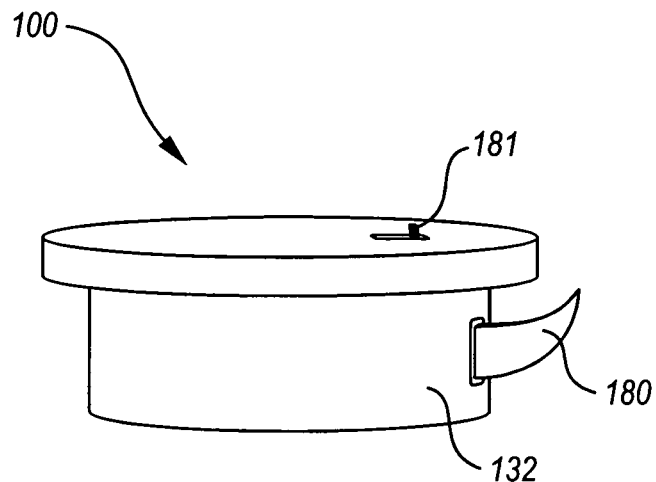
FIG. 9A illustrates an exemplary stimulator with a securing cog that extends from the main housing according to principles described herein.
Figure 9B:
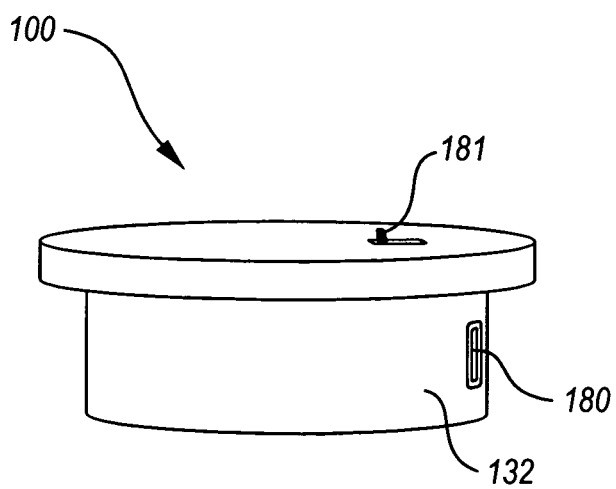
FIG. 9B shows the lever in the second position and the cog retracted into the main housing according to principles described herein.

If desired, the stimulator (100) may be secured in the burr hole (106) with a number of different securing devices. For example, FIG. 9A illustrates an exemplary stimulator (100) with a securing cog (180) that extends from the main housing (132). A lever (181) or other mechanism that controls the position of the cog (180) may be included on the top surface of the stimulator (100). When the cog (180) is in an extended position, as shown in FIG. 9A, it may engage and penetrate into the cranium at the sidewall of the burr hole (106; FIG. 2) to secure the stimulator (100) in place in the burr hole (106; FIG. 2). When it is desired to adjust the position of the stimulator (100) or remove the stimulator (100) from the burr hole (106; FIG. 2), the lever (181) may be moved to a second position to retract the cog (180) away from the sidewall of the burr hole (106; FIG. 2) and into the main housing (132). FIG. 9B shows the lever (181) in the second position and the cog (180) retracted into the main housing (132). It will be recognized that the securing cog (180) and lever (181) are merely illustrative of the many different securing devices and related mechanisms that may be used to secure the stimulator (100) in the burr hole (106; FIG. 2).

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system comprising:
    a stimulator including a housing having opposing top and bottom surfaces and configured to be at least partially disposed within a burr hole in a cranium of a patient, electronic circuitry contained within said housing and configured to generate an electrical stimulus, a first number of electrical contacts and a first registration element disposed on said bottom surface of said housing, and a hollow lumen extending through said housing and terminating in said opposing surfaces, wherein said lumen has a longitudinal axis, and said opposing surfaces of said housing are respectively located at opposite ends of said longitudinal axis;
a stimulating member having a lead and a number of electrodes disposed on said lead for applying said electrical stimulus to a stimulation site within said patient;
a connector member coupled to a proximal portion of said stimulating member, said connector member having opposing top and bottom surfaces, a hollow lumen, a second number of electrical contacts and a second registration element disposed on said top surface of said connector member, wherein said first and second registration elements correspond to each other to align said first and second numbers of electrical contacts with each other; and
a coupling member configured to extend through said lumens of said stimulator and said connector member and apply opposing forces to said housing and said connector member to secure said stimulating member to said housing, such that said electrical contacts of said stimulator are electrically coupled to said electrical contacts of said connector member.

2. The system of claim 1, wherein said stimulator further comprises a lip member coupled to said housing and configured to extend a distance along an outer surface of said cranium, wherein said lip member is configured to prevent said stimulator from falling into said cavity formed by said cranium.

3. The system of claim 1, wherein said coupling member comprises:
a shaft member configured to extend through said lumens of said stimulator and said connector member; and
a fastening device configured to secure said shaft member to said housing and said connector member.

4. The system of claim 3, wherein said fastening device comprises at least one or more of a nut, a clamp, and a rivet.

5. The system of claim 1, further comprising a securing device configured to secure said stimulator in said burr hole.

6. The system of claim 1, wherein said coupling member is further configured to hermetically couple said stimulating member to said housing.

7. A method of using the system of claim 1, comprising:
implanting said stimulating member and connector member within said patient;
implanting said stimulator within said burr hole; and
extending said coupling member through said lumens of said stimulator and said connecting member to secure said stimulating member to said housing.

8. The method of claim 7, further comprising securing said stimulator within said burr hole.

9. The method of claim 7, further comprising applying said at least one stimulus to a stimulation site within said patient via said stimulating member.

10. The system of claim 2, further comprising a communication port disposed on a top surface of said lip member for communicating with an external device.

11. The system of claim 1, wherein said first registration element comprises one of a depression and a protrusion corresponding to said depression a different one of said depression and said protrusion.

12. The system of claim 1, further comprising:
a third registration element disposed on a top surface of said coupling member; and
a fourth registration element disposed on said bottom surface of said connector member, wherein said third and fourth registration elements correspond to each other.

13. The system of claim 1, wherein said connecting member comprises a lumen extending therethrough, and said coupling member configured to extend through said lumen of said connector member to secure said connector member to said housing.

14. The system of claim 1, wherein said coupling member is configured to secure said stimulating member to said housing while said stimulating member is disposed within said patient.

15. The system of claim 13, wherein said coupling member is configured to press said top surface of said connecting member against said bottom surface of said housing to secure said connector member to said housing.

16. The system of claim 1, wherein said opposing surfaces of said housing are substantially parallel to each other and substantially perpendicular to said longitudinal axis of said lumen.

17. The method of claim 7, wherein said coupling member comprises a shaft member and a fastening device, the method further comprising:
extending said shaft member through said lumens of said stimulator and said connector member; and
fastening said fastening device to said shaft member to secure said stimulating member to said housing.

18. The method of claim 17, wherein said fastening device is fastened to said shaft member after said stimulating member and said connector member are implanted within said patient.

* * * * *